(12) United States Patent
Edgell

(10) Patent No.: US 7,950,395 B2
(45) Date of Patent: May 31, 2011

(54) RESTRAINING SYSTEM

(75) Inventor: Lewis R. Edgell, Midlothian, VA (US)

(73) Assignee: Lewis R. Edgell, Midlothian, VA (US)

( * ) Notice: Subject to any disclaimer, the term of this patent is extended or adjusted under 35 U.S.C. 154(b) by 537 days.

(21) Appl. No.: 11/980,680

(22) Filed: Oct. 31, 2007

(65) Prior Publication Data

US 2009/0107418 A1    Apr. 30, 2009

(51) Int. Cl.
*A61B 19/00* (2006.01)
(52) U.S. Cl. .......................................... 128/869; 602/32
(58) Field of Classification Search .................. 128/869, 128/882; 602/32–36
See application file for complete search history.

(56) References Cited

U.S. PATENT DOCUMENTS

| | | | | |
|---|---|---|---|---|
| 1,021,688 A | * | 3/1912 | Le Jeune | 602/33 |
| 1,188,711 A | * | 6/1916 | Wilting | 602/39 |
| 3,458,656 A | * | 7/1969 | Sewerin | 73/592 |

* cited by examiner

*Primary Examiner* — Michael A. Brown
(74) *Attorney, Agent, or Firm* — Davidson Berquist Jackson & Gowdey, LLP

(57) ABSTRACT

A mechanical restraining system for use in situations where it is desirable to restrain a detainee, such as a prisoner, psychiatric patient or accused criminal defendant, while minimizing the ability of the public or certain courtroom participants to readily observe that the detainee has been placed in or is being held by some type of restraining device.

16 Claims, 3 Drawing Sheets

RESTRAINING SYSTEM

FIELD OF THE INVENTION

Mechanical restraining systems, and more particularly, a restraining system for use in a variety of situations where it is desirable to restrain an individual, as well as where it might be desirable to hide the use or presence of a restraining device, where that individual is a detainee such as a prisoner, a mentally ill or a psychotic patient, a potential committee, an arrestee, a criminal defendant, multiple prisoners or like individuals, or any one who is considered to be or may become violent, threatening or who might try to escape custody.

BACKGROUND AND SUMMARY OF INVENTION

During certain trial or court proceedings or other hearings, the use of visible restraining devices or systems is often undesirable because it may adversely affect the presumption of innocence accorded a criminal defendant or may otherwise unnecessarily stigmatize a defendant or detainee in the eyes of the public or jury. However, there is a risk that any detainee may be or become violent, dangerous or attempt unpredictable actions that would be a threat to the public, to courtroom personnel or to spectators or to witnesses. Failing to use a restraining device on the detainee therefore creates a risk that the detainee or defendant will assault and inflict injury on police officials, court officials or innocent bystanders. Further, escorting or attending to the detainee while in the courtroom or hearing room places a burden on the already overburdened state, local and federal law enforcement departments or offices who are handling more prisoners with less personnel.

Thus, to accommodate the need for public safety as well as the desire not to unnecessarily stigmatize a detainee, it is desirable to use a restraining device that is capable of sufficiently immobilizing an individual, but is also capable of being hidden or disguised from a judge, jury or members of the public to avoid adversely affecting the presumption of innocence or other stigma.

Other restraining devices have been proposed, such as, for example, a restraint chair as disclosed in U.S. Pat. No. 5,758, 892. However, the chair disclosed in the '892 patent does not hide the fact that the prisoner or detainee is restrained. Prisoner security devices have also been disclosed which relate to transporting a prisoner or other detainee in a vehicle. For example, Pub. Nos. US 2006/0225943 A1 and US 2006/0061198 disclose a device that is intended to be used in a vehicle to restrain a prisoner using a retractable strap that attaches to the prisoner's handcuffs or other restraining apparatus and holds the prisoners' hands behind him in a vehicle.

There have also been electrical devices disclosed that may be worn by a prisoner beneath clothing and, thus, hidden from the public eye. For example, U.S. Pat. No. 4,943,885, discloses a device worn beneath a prisoner's clothing wherein the device can be activated remotely to attempt to control the prisoner by using either an electrical impulse or a discharge of some noxious gas such as tear gas. These devices may, however, not be effective on certain prisoners who can withstand the controlling mechanism that may be implemented and, moreover, should the device fail to work as designed, there would be effectively no restraining device in use. This type of device also suffers from the potential adverse consequences the noxious gas may have on those nearby who are unintended victims.

The restraining approach disclosed herein overcomes the deficiencies of the devices discussed above. The restraining system is directed to a mechanical restraining device that is not generally or easily visible to the judge or jury or other hearing officer and which further permits the detainee to stand, sit and, optionally, move within some limited range, without bringing undue attention to the restraint system.

The restraining system includes a restraining security device, such as a rod assembly, spaced above the floor or some other type of surface an appropriate distance to permit the detainee to comfortably place his or her feet on the floor or surface. The restraining system is capable of being used with restraint devices known in the art, such as, for example, a leg iron. In these cases, the leg iron can be securely attached to the prisoner's left or right leg, while the other leg iron is securely attached to the rod assembly. Alternatively, the restraining system may optionally include one or more restraint devices already present, either permanently attached or removeably attachable, capable of permitting a detainee to be secured to the rod assembly. The rod assembly or restraining security device can be secured to the floor, either permanently or removeably. If the rod assembly is removeably secured to the floor, it may optionally include security measures, such as requiring a code or a key, before releasing the rod assembly, intended to prevent detainees from becoming free. Alternatively, the rod assembly can be secured to the table. In any event, the rod assembly should be located below the counsel table at which the detainee or prisoner or other person for whom it is desirable to restrain, will be seated.

The rod assembly can me made of any sturdy material such as, for example, metal, including brass, steel, other metals, wood, reinforced plastic, or such other material as is known in the art and is sufficiently sturdy to serve the purpose of restraining a detainee. The rod assembly can be fastened to either the table or a surface, such as the floor, by means known to those of skill in the art, including, for example, the use of hardened steel screws, bolts or other devices/methods known to those of skill in the art. Where, for example, the surface or the table frame is metal, the rod assembly may be attached by welding.

In accordance with another aspect of the restraining system, the rod assembly may further include a covering of some type intended to reduce or dampen noise that can be made by the leg iron coming into contact with and/or moving against or along the rod assembly. The covering could be formed directly on the rod assembly, be added as a separate item and could be a chemical or foam material, rubber, cloth or some other material known to those of skill in the art to reduce noise, alone or in combination with those or other sound deadening materials. In accordance with yet another aspect of the restraining system, the table beneath which the rod assembly was mounted could further include a curtain or screen, for example held in place by snaps, Velcro or other removable fastening technique or mechanism, to limit or prevent the viewing of the restraining device on the detainee by the jury or judge or others whom it may be desirable to shield from view.

Alternatively, such detainees also need to be transported to and from various locations and it is also essential to positively restrain such individuals during periods of transport.

BRIEF DESCRIPTION OF THE DRAWINGS

For a more complete understanding of the present restraining system and the advantages thereto, the drawings set forth an illustrative embodiment that should not be considered as limiting the scope of the restraining system and reference is made to the following Detailed Description of the Invention in conjunction with the accompanying drawings wherein.

DETAILED DESCRIPTION OF THE INVENTION

Figure 1:
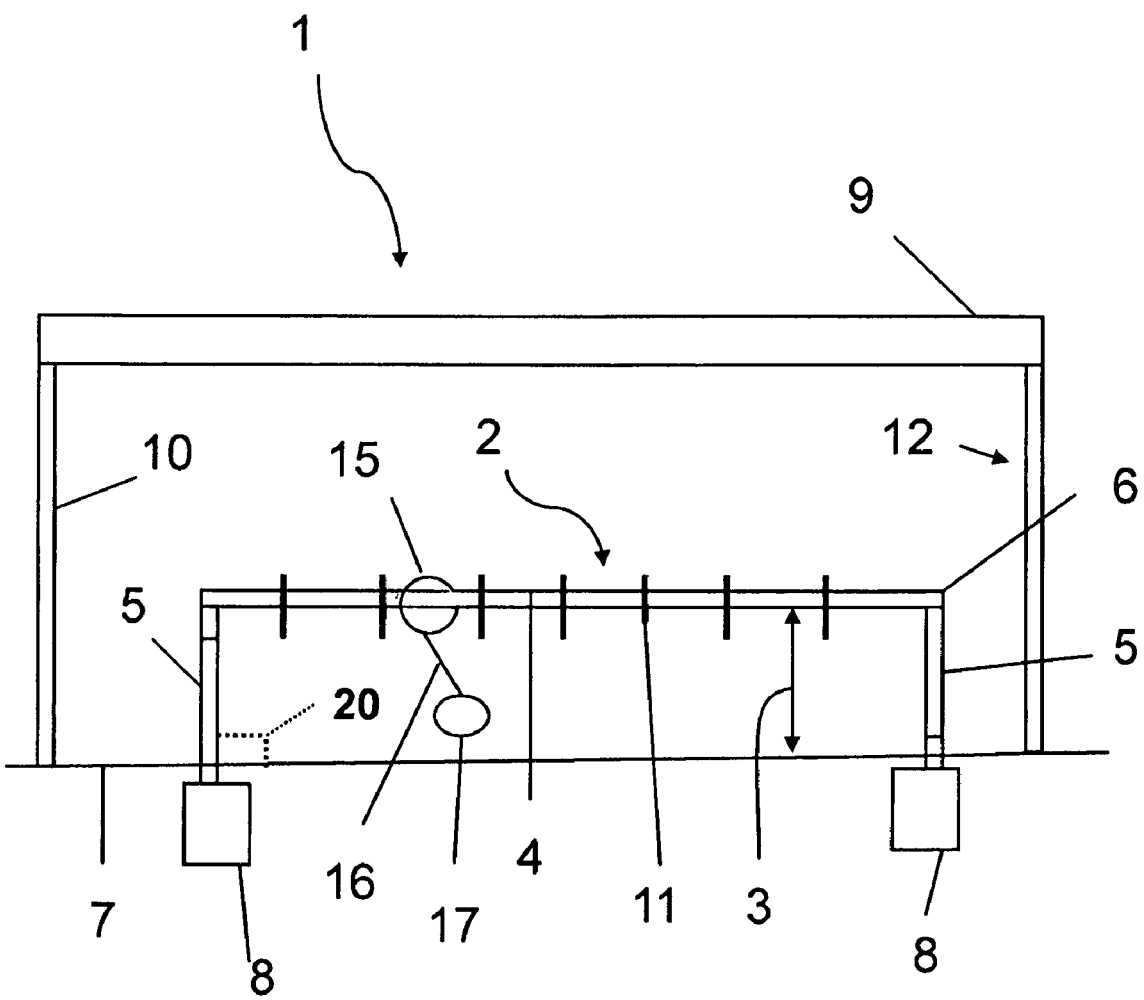
FIG. 1 is a front elevational view of a court room or hearing room table with the restraining system mounted there under.

The restraining system 1, as shown in FIG. 1, includes a rod assembly 2 that is spaced from the floor some appropriate distance or gap 3. The gap 3 can be any distance that permits, for example, the security personnel to secure one or more detainees and that further permits a detainee's feet to rest on a surface, such as the floor, under or near the rod assembly 2 while maintaining leg irons or other leg restraint or tethering devices, shown at 15 for a rod connection, at 17 for a leg connection and an interconnecting member 16 there between, that can be attached both to the rod assembly 2, at 15, and the detainee's leg by the restraint 17. By way of nonlimiting example only, the distance 3 may fall within the range of about four to about ten inches from the surface.

The rod assembly 2 is comprised of a horizontally extending rod portion 4 and a pair of opposing end posts 5. The horizontally extending rod portion 4 and the pair of opposing end posts 5 may be a one piece U shaped body or, alternatively, may be separate components that are securely connected or joined together in any number of ways as would be known to those in the art. For example, each end of the horizontal rod portion 4 may be joined to the top end 6 of an end post 5 by the use of screws, bolts, elbow joints, U shaped joints or some other bracketing device, connector or attaching mechanism known in the art. Alternatively, the horizontal rod portion 4 may be more permanently affixed to the top end 6 of the end post 5 by the use of welding or the like.

The horizontally extending rod portion 4 is capable of receiving or holding a leg restraint device, such as, for example, a leg iron, tether or the like, that is already being used to restrain a detainee. Alternatively, one, or more than one, leg restraint device 15 may be coupled with the horizontally extending rod portion 4 of the rod assembly 2 so that leg restraint device 17 of the restraining system 1 is capable of receiving a portion of the leg of a detainee who does not have leg restraints available, thereby securing the detainee to the rod assembly 2. In this case, the leg restraint device 15 or devices may be either permanently affixed to, or removeably coupled to, the horizontally extending rod portion 4.

The two end posts 5 may be secured to the surface 7, such as a floor, in the room, which can be, for example, a courtroom or other hearing room. Any means known in the art to securely attach the end posts 5 to the surface 7 is contemplated by the restraining system 1. The end posts 5 can be attached to the surface 7 by using recessed secure floor anchors 8 that could be embedded within a concrete floor or secured by screws in a recess otherwise provided in floor 7. The recessed floor anchors 8 may be covered by a floor plate, which can be also locked to further secure and prevent tampering with the restraining system 1. The end posts 5 may be removeably coupled to the surface 7 by the use of floor anchors 8 which may optionally include security measures that prevent the unintentional removal of the end posts 5 which could result in freeing the detainee. For example, a security code or special key may be required to release the end posts 5 from the coupling mechanism contained within the recessed floor anchor 8. The restraint system 1 is preferably located under the table 9 at which the accused or detained person will be seated. Further, end posts 5 could be directly secured to floor 7 by a flange 20, shown in dotted line, that could be directly secured to post 5, by welding or some tamper proof securing screw or fastener. Flange 20 could then be secured to floor 7 by steel screws or other anchoring device that would be removable by court room personnel. This would allow for removal of the flange and the attached rod assembly.

Alternatively, the restraining system 1 can be secured directly to the frame of the table 9 by securing the rod 2 directly to the table legs 10 located on the left and right back side of the table 9. It may be necessary to brace or reinforce the table frame to ensure the rod assembly 2 will remain stable.

The rod assembly 2, or portions thereof, is preferably made of a solid material, such as, for example, metals, including brass, iron, nickel or steel or wood, or manmade materials including, but not limited to plastics, reinforced plastics, polycarbonates or such other material that is sufficiently strong enough to withstand attempts by the detainee to break free. The rod assembly 2 can be of varying lengths and is preferably of sufficient length to permit the detainee, or multiple detainees, to move along the approximate length of the table 9 under which the rod assembly 2 is placed, or to permit the detainee to be placed at varying locations at the table 9. For example, the rod assembly 2 can generally be eight feet long or less to accommodate a normal size table 9 in a courtroom or hearing room, but there could be segmented sections of the rod assembly 2, especially if the table was long.

The rod assembly 2 can optionally include spacers 11, shown in FIG. 1, that can be used to limit or monitor the movement of the detainee. Optionally, the spacers 11 can permit more than one detainee to be attached to the rod 2 at the same time, for example, in the case of multiple defendants. The spacers 11 can be formed as an integral part of the rod assembly 2 or the horizontally extending rod portion 4. Alternatively, the spacers 11 can be separate components that are removeably attached to the rod assembly 2 yet which fit snugly around the rod assembly 2. The spacers 11 should be sturdy and not movable by a detainee. The spacers 11 can be formed from a variety of materials, including the same materials comprising the rod assembly 2, including hard, unyielding materials such as metals or mixtures of metals, resins, wood, thermoplastics, reinforced plastics or polycarbonates or other strong or reinforced material. The spacers 11 can be, for example, rings that extend around rod 4, bars that extend outwardly from rod 4 or unshaped members that protrude above or below and along the horizontal rod portion 4 of the rod assembly 2 a sufficient length, so that regardless of what form the spacer takes it will prevent the leg iron or other restraining device from sliding over, beyond or around the spacer 11. While the spacers 11 have been shown in FIG. 1 as each being the same type, size and shape, the spacers 11 could be different from one another in shape and/or type or each spacer 11 could be the same or similar in type and/or shape, but differ in size.

Figure 2:
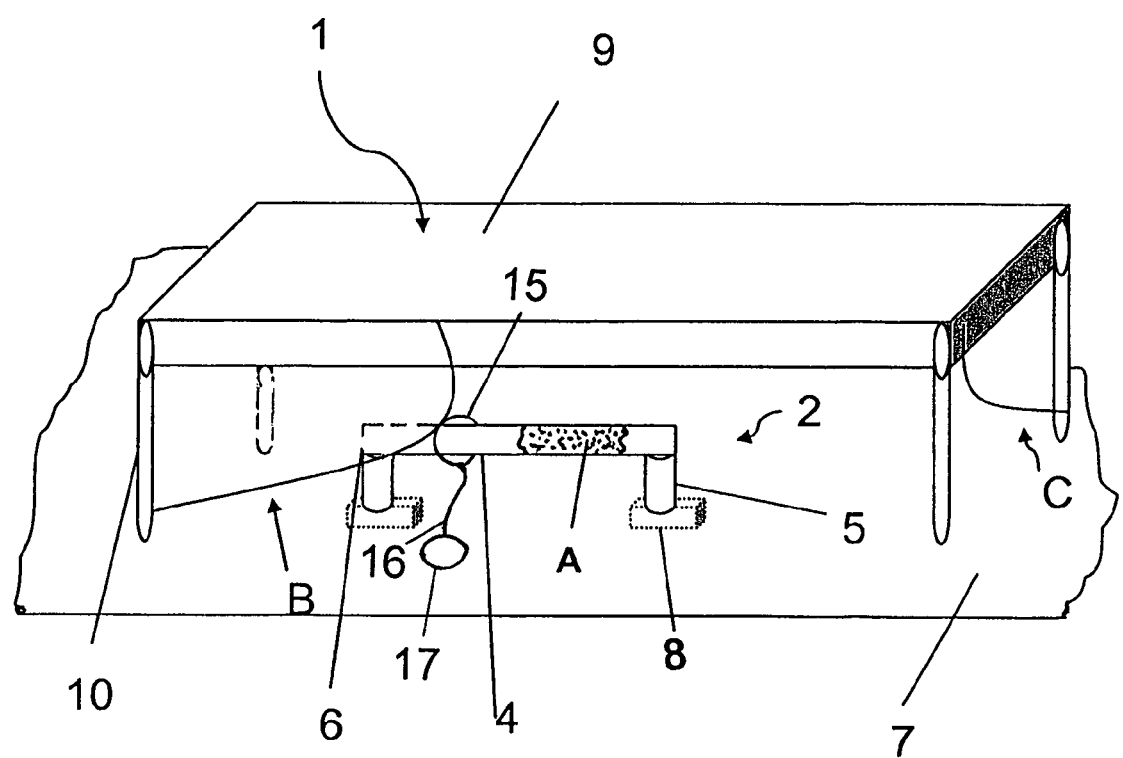
FIG. 2 is perspective view of a table with the restraining system mounted there below.

In accordance with another aspect of the restraining system, the rod assembly 2 may further include a covering A, as shown in FIG. 2, of some type intended to prevent or reduce the noise made by the leg iron or other leg restraint device as it moves along or relative to the rod assembly 2. The covering may comprise a chemical coating (such as a molded foam layer), rubber, cloth or some other material known to those of skill in the art to reduce or dampen noise.

In accordance with yet another aspect of the restraining system 1, as shown in FIG. 2, the detainee's table 9 may include a screening device, such as an opaque table front or panel B and/or side panels C that limit or eliminate the ability of those standing in front or to the side of the table 9 to view underneath the table 9. Alternatively, the table 9 may have screening in the form of a fabric or other cover, fixed or removably attached to the front of the table 9 and, optionally, one or both sides 12 of the table 9. As noted above, the screening is intended to limit, if not eliminate, the view of the restraining device on the detainee by the jury or judge or others from whom it may be desirable to shield the restraining device from view. The screening may be permanently affixed to the table 9 or detachable from the table 9. The screening may be affixed or attached to the table in any number of ways known in the art such as, for example, by Velcro, snaps, screws, nails, bolts, hanging rods, or the like. The screening may be similar to a curtain and may be made of cloth, plastic or some other natural or manmade material.

Figure 3:
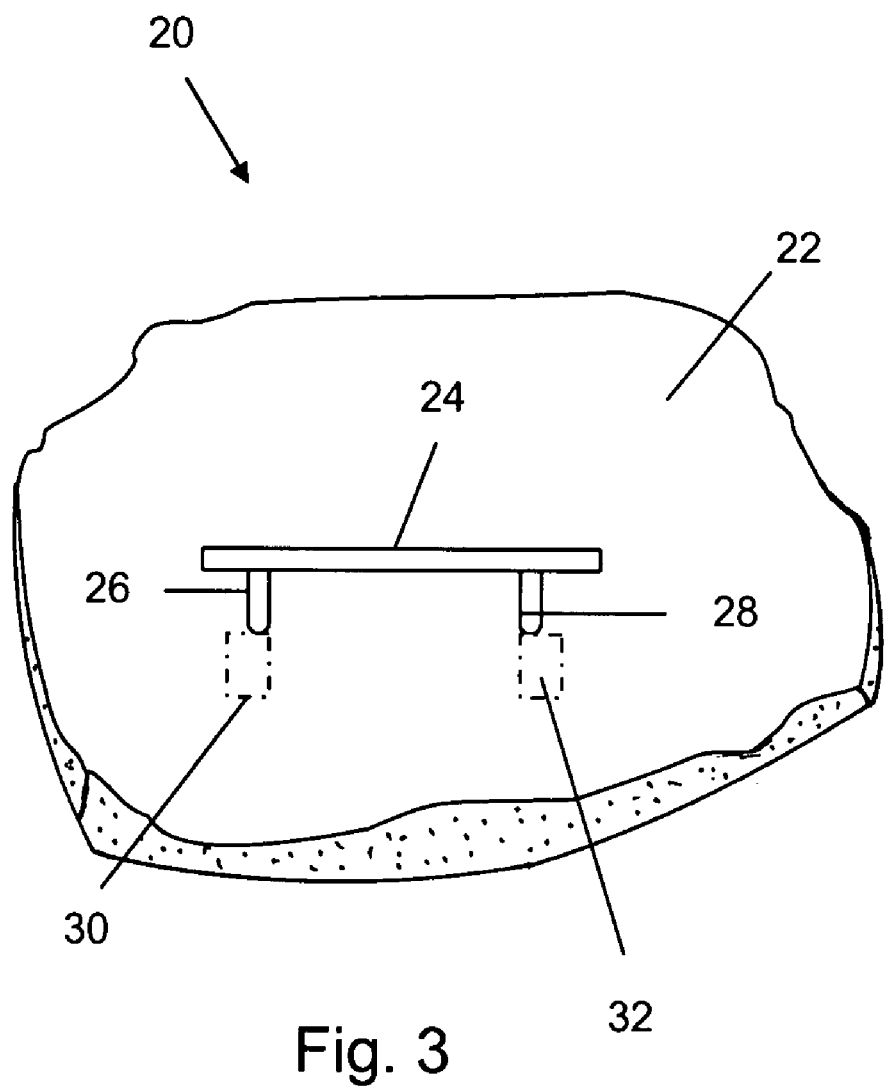
FIG. 3 is partial perspectives of a restraining system mounted to a floor segment.

FIG. 3 shows an alternative version of the restraining system 20 for use in transport vehicles, such as vans, busses, or in trains, airplanes or other forms of transportation.

A floor segment is shown at 22 and anchor mechanisms 30 and 32, respectively, are shown as being embedded within floor 22. A pair of upstanding end posts 26 and 28 are secured to anchor 30 and 32, respectively, and their opposite ends are welded or otherwise secured to a horizontally extending rod portion 24 to which an individual is then connected by a restraint device as disclosed previously.

End posts 26 and 28 along with rod 24 will also be constructed from metal or other material that cannot be broken or moved to the point where the individual's restraint that has been connected to rod 24 cannot itself be moved.

While the present invention and its advantages have been described in detail in connection with what is presently considered to be the most practical and preferred embodiment, it should be understood that the present invention should not be limited to the disclosed embodiment, but on the contrary, is intended to cover various changes, substitutions and alterations therein, including in the configuration and assemblage of the various parts comprising the present invention, without departing from the spirit and scope of the invention as defined by the appended claims, which changes, substitutions and alterations are intended to be embraced therein.

What is claimed is:

1. A restraining system for a detainee comprising:
   a rod assembly anchored to a surface, the rod assembly comprising a horizontally extending rod portion having opposing first and second ends and an end post secured to each of the opposing first and second ends of the rod portion, said end posts each being secured to the surface and to space the rod portion away from the surface, and further including a detainee restraining assembly comprised of a first restraint member being releasably locked on the detainee, a second restraint member being releasably secured onto the rod portion so as to be slidable there along during use and an interconnecting structure between the first and second restraint members, wherein said rod assembly will limit movement of the detainee wherein the horizontally extending rod portion further includes a sound dampening cover thereon.

2. The restraining system of claim 1, wherein the surface is a floor.

3. The restraining system of claim 1, wherein the restraining system is located in the floor of a hearing room and beneath a table.

4. The restraining system of claim 3, wherein the horizontally extending rod portion includes a plurality of spacers fixed thereto.

5. The restraining system of claim 4, wherein the spacers are capable of limiting the horizontal range of movement of the detainee restraint assembly along the rod portion.

6. The restraining system of claim 1, wherein the first restraint member is locked onto the detainee's leg.

7. The restraining system of claim 1, wherein the restraining system is located in the floor of a transport vehicle.

8. The restraining system of claim 1, wherein the horizontally extending rod portion and the opposing end post portions comprise a single U shaped member.

9. The restraining system of claim 1, wherein the rod assembly is detachable from the surface.

10. A restraining system comprising:
    a rod assembly anchored to a surface, the rod assembly comprising a horizontally extending rod portion having opposing first and second ends, said rod portion having a sound dampening cover thereon, and an end post coupled to each of the opposing first and second ends of the rod portion and to the surface to space the rod portion above the surface, and a detainee restraining assembly comprising a detainee restraint member secured to a member slidingly secured onto the rod portion so that the detainee has limited mobility along the length of the rod portion when the restraining system is in use.

11. The restraining system of claim 10, wherein the rod portion of the restraining system is located in a court room and is secured to a portion of a floor surface located below a table at which a restrained individual will sit.

12. The restraining system of claim 11, further including screening device positioned adjacent the rod portion.

13. The restraining system of claim 10, wherein the horizontally extending rod portion includes a plurality of spacers fixed thereto.

14. The restraining system of claim 13, wherein the spacers are capable of limiting the horizontal range of movement of the detainee restraining assembly.

15. The restraining system of claim 10, wherein detainee restraining assembly is coupled to a leg of the detainee.

16. The restraining system of claim 10, wherein the horizontally extending rod portion and the opposing end posts comprise a single member.

* * * * *

UNITED STATES PATENT AND TRADEMARK OFFICE
CERTIFICATE OF CORRECTION

PATENT NO. : 7,950,395 B2
APPLICATION NO. : 11/980680
DATED : May 31, 2011
INVENTOR(S) : Lewis R. Edgell Page 1 of 1

It is certified that error appears in the above-identified patent and that said Letters Patent is hereby corrected as shown below:

On the Title Page, Item (75)

The address of the Inventor, Lewis R. Edgell, is erroneously listed as "Midlothian, VA" and should be corrected to be "6113 Friesian Terrace, Moseley, VA 23120."

Signed and Sealed this
Twenty-fifth Day of March, 2014

Michelle K. Lee
*Deputy Director of the United States Patent and Trademark Office*